United States Patent [19]

Smith

[11] 4,080,366
[45] Mar. 21, 1978

[54] CONVERSION OF ESTERS OF 1,4-BUTANEDIOL TO TETRAHYDROFURAN

[75] Inventor: William Edward Smith, Schenectady, N.Y.

[73] Assignee: General Electric Company, Pittsfield, Mass.

[21] Appl. No.: 635,729

[22] Filed: Nov. 26, 1975

[51] Int. Cl.² .......................................... C07D 307/08
[52] U.S. Cl. ................................................ 260/346.11
[58] Field of Search ................................ 260/346.1 R

[56] References Cited
U.S. PATENT DOCUMENTS 2,251,835  8/1941  Reppe et al. ................... 260/346.1 R

FOREIGN PATENT DOCUMENTS 2,062,950  7/1971  Germany ....................... 260/346.1 R
1,170,222  11/1969  United Kingdom .......... 260/346.1 R

OTHER PUBLICATIONS

Murata et al., Chem. Ab., vol. 78, (1973), 147773.

Primary Examiner—Natalie Trousof
Assistant Examiner—Bernard Dentz
Attorney, Agent, or Firm—William F. Mufatti

[57] ABSTRACT

An improved process for producing tetrahydrofuran by dehydroacyloxylation or hydrolysis-dehydroacyloxylation of carboxylic acid mono- and diesters of 1,4-butanediol, the improvement comprising carrying out said process in the presence of a tungsten oxide catalyst.

9 Claims, No Drawings

CONVERSION OF ESTERS OF 1,4-BUTANEDIOL TO TETRAHYDROFURAN

This invention relates to an improved process for producing tetrahydrofuran by dehydroacyloxylation of hydrolysis-dehydroacyloxylation of carboxylic acid mono- and diesters of 1,4-butanediol, the improvement comprising carrying out said process in the presence of a tungsten oxide catalyst.

BACKGROUND OF THE INVENTION

It is known in the art that tetrahydrofuran may be produced by a number of different methods, the more prominent among them the dehydration of 1,4-butanediol and the catalytic hydrogenation of furan. Most tetrahydrofuran is, in fact, manufactured in a multi-step sequence starting with the reaction of acetylene and formaldehyde in the presence of a cuprous acetylide complex to form butynediol. The butynediol is hydrogenated to butanediol, which is dehydrated to tetrahydrofuran as indicated above.

In addition, tetrahydrofuran can be prepared by catalytic hydrogenation of maleic, fumaric and succinic acids, their respective anhydrides and ester derivatives, and butyrolactone.

All of these methods involve the use of hazardous or expensive materials, and catalysts that are expensive in some instances and easily poisoned in others.

The liquid phase conversion of 1,4-butanediol carboxylate ester derivatives to tetrahydrofuran in the presence of strongly acidic catalysts and water has been described by Kohll in British Pat. No. 1,170,222 and by Ono et al, in German Offenlengungsschrift 2,062,950. As disclosed in copending applications of William E. Smith, Ser. Nos. 623,904 and 623,905 (now U.S. Pat. Nos. 4,011,244 and 4,010,171 respectively) filed on Oct. 20, 1975, both titled *A Process for Preparing Tetrahydrofuran,* and assigned to the same assignee as the present invention, tetrahydrofuran can be advantageously produced by vapor phase dehydroacyloxylation or hydrolysis-dehydroacyloxylation of carboxylate esters of 1,4-butanediol promoted by such catalysts as alumina, silica and silica-alumina.

Tetrahydrofuran is a useful solvent for natural and synthetic resins and is a valuable intermediate in manufacture of a number of chemicals and plastics.

DESCRIPTION OF THE INVENTION

It has been discovered that tetrahydrofuran can be produced from carboxylic acid mono- and diesters of 1,4-butanediol in an improved dehydroacyloxylation and hydrolysis-dehydroacyloxylation process which employs a class of heterogeneous catalysts based on the partly reduced oxide or oxides of tungsten. The method is characterized by high reaction efficiency; the catalysts are extremely active, selective and long-lived. Yields of tetrahydrofuran and acetic acid are essentially quantitative in both liquid phase and vapor phase modifications.

The catalysts that may be used within the scope of the instant invention include all tungsten oxide compounds, including tungstic oxide, tungstic acid, partly reduced tungsten oxide and tungstic acid derivatives, and mixtures thereof. The scope of the instant invention also includes the use of active support materials such as alumina, silic, silica-alumina and the like in combination with the tungsten oxide compounds, as well as inert support materials.

The partly reduced "blue oxide" of tungsten has been recognized for many years as a powerful agent for dehydrating alcohols to olefins. This substance was until more recent years formulated as $W_2O_5$; it is now commonly accepted as having the composition $W_{20}O_{58}$.

The process as applied to monoesters of butanediol is illustrated in Equation 1 for the dehydroacetoxylation of 4-acetoxybutanol:

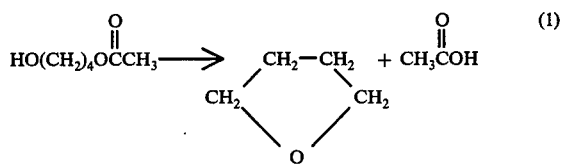

This transformation can be brought about under anhydrous conditions. The conversion of diesters of 1,4-butanediol, however, does require the presence of water. For example, 1,4-butanediol diacetate is not converted to tetrahydrofuran unless it is first hydrolyzed to 4-acetoxybutanol as illustrated in Equation 2. The formation of tetrahydrofuran from 1,4-butanediol diacetate is thus a composite of the hydrolysis and dehydroacetoxylation processes (Equation 3).

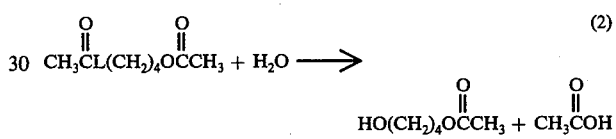

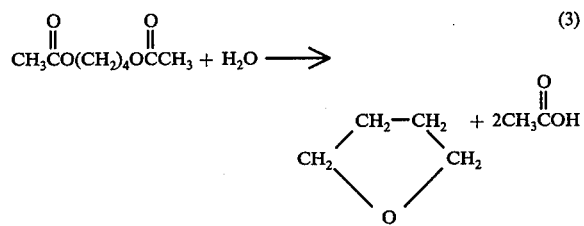

In the vapor phase modification of the disclosed process, the active catalyst may be prepared in place by reducing a bed of supported or unsupported tungstic acid ($WO_3$) in a stream of hydrogen. In the liquid phase modification, the catalyst may be prepared in situ by heating tungstic oxide, tungstic acid ($H_2WO_4$), or either of these substances compounded with a support such as alumina, silica, or the like in the presence of the reactants, optionally in a hydrogen atmosphere. In both the vapor phase and liquid phase methods, the active catalyst is a partly reduced tungsten oxide.

When the tungsten oxide is supported on alumina or silica or the like, a synergistic activting effect may be achieved. Thus a catalyst prepared from a composition of 10% tungstic oxide and 90% aluminum oxide is substantially more active than one derived from tungstic oxide itself. Alumina, silica, silica-alumina and other such oxide supports are themselves catalysts for the dehydroacyloxylation and hydrolysis-dehydroacyloxylation reactions, but are substantially less active than the partly reduced tungsten oxide, supported or unsupported.

The carboxylic acid esters of 1,4-butanediol suitable for use in the disclosed process are those in which the carboxy function contains from one to six carbon atoms. A preferred ester is 4-acetoxybutanol. In a preferred embodiment, the 4-acetoxybutanol is used in admixture with 1,4-butanediol diacetate, 1,4-butanediol and the corresponding monoacetate, diacetate and diol derivatives of 1,2-butanediol and 2-methyl-1,3-propanediol. As disclosed in copending application Ser. No. 581,266, filed on May 27, 1975, entitled *A Process for Preparing Tetrahydrofuran* and assigned to the same assignee as the present invention, and now U.S. Pat. No. 4005113 such a mixture can be derived from propylene by way of allyl acetate and a hydroformylation-hydrogenation sequence.

At least one mole of water is required for each mole of diester to be converted. Generally, a ratio in the range of from one to about 30 moles of water per mole of diacetate is sufficient to effect the desired conversion.

The temperature at which the disclosed process can be carried out varies from about 175° C to about 325° C. Preferably, the dehydroacyloxylation or hydrolysis-dehydroacyloxylation is carried out in the temperature range of 200° C to about 275° C. The maximum depends upon destruction of the product, olefin formation occurring from the 1,4-derivatives under too rigorous conditions.

In a preferred embodiment, a bed of a tungstic oxide catalyst is reduced in place by heating under a hydrogen stream, and a feedstock of which 4-acetoxybutanol is the principal component is passed through with a hydrogen carrier gas at about 250° C. The conversion to tetrahydrofuran and acetic acid is complete in a single pass at a liquid hourly space velocity (LHSV) as high as 1.0.

Well known techniques may be employed to obtain the tetrahydrofuran in pure and anhydrous form.

DESCRIPTION OF THE PREFERRED EMBODIMENT

The following examples are set forth to illustrate more clearly the principle and practice of this invention to those skilled in the art. Unless otherwise specified, where parts or percents are mentioned, they are parts or percents by weight.

The vapor phase processes to be described were carried out using a 20 mm ID × 30 cm effective length vertical hot tube reactor (70 cc effective volume), constructed from heavy wall glass, with 24/40 male and female joints. Vigreaux points were indented just above the male joint to support catalyst pellets. Thermocouple leads were fastened into three other Vigreaux indentations at points along the length. Briskheat glass insulated heating tapes were wound onto the tube, covered with glass wool and glass tape, and connected to separate variable transformers. The tube exit was connected by a gooseneck (also heated) to an efficient condenser and collection vessel. An electrically heated three-necked flask served as the evaporator, with the reactants added through a side neck by a syringe pump. A hydrogen stream (one bed volume per minute) served as the carrier gas.

The liquid phase processes to be described were carried out using an Autoclave Engineers 300 cc Magnedrive autoclave.

EXAMPLE 1

The tube reactor charged with 162 grams (70 ml) of Harshaw tungsten catalyst WO602, ⅛ inch pellets containing 95% $WO_3$, was employed with crude butanediol acetate composed of the monoacetates of 1,4-butanediol, 1,2-butanediol and 2-methyl-1,3-propanediol as well as their respective diacetate and diol disproportionation products. The feedstock contained 5.86 milliequivalents of 1,4-butanediol and acetate derivatives per gram, 0.254 milliequivalents of the 1,2-butanediol and acetate derivatives per gram, and 0.544 milliequivalents of 2-methyl-1,3-propanediol and acetate derivatives per gram, as determined by glpc analysis of a completely acetylated sample. Operation at 250° C with the hydrogen carrier gas and an LHSV of 0.5 afforded a steady state effluent containing (molar proportions) tetrahydrofuran (1.0), acetic acid (0.91), 1,4-butanediol diacetate (0.095), 2-methyl-1,3-propanediol diacetate (0.041), methallyl acetate (0.040), crotyl acetate (0.004), n-butyraldehyde (0.005), crotonaldehyde (0.009), and a small amount of water. A trace of isobutyraldehyde was also detected. No 1,2-butanediol or its acetate derivatives were found. This analysis was accomplished using a combination of standard glpc, glpc-mass spectrometry and nmr techniques.

EXAMPLE 2

The process was operated as described in Example 1 using a feedstock composed of the crude butanediol acetate and water in 1:1 weight ratio. The steady state effluent in this case was composed of (molar proportions) tetrahydrofuran (1.0), acetic acid (1.15), 1,4-butanediol diacetate (0.08), 4-acetoxybutanol (0.006), 2-methyl-1,3-propanediol diacetate (0.014), 3-acetoxy-2-methylpropanol (0.010), methallyl acetate (0.01), crotyl acetate (0.01), crotonaldehyde (0.01), n-butyraldehyde (0.06) and water. Again, no 1,2-butanediol derivatives were detected.

EXAMPLE 3

A mixture of 150 grams of the crude butanediol acetate described in Example 1, 30 ml of water and 1.5 grams of tungstic acid ($H_2WO_4$) was heated in the stirred autoclave at 250° C under 500–700 psi of hydrogen for two hours. Analysis of the reaction products shows that about 85% of the 1,4-butanediol derivatives had been converted to tetrahydrofuran, with liberation of about the corresponding amount of acetic acid. The insoluble blue "$W_{20}O_{58}$" was the isolated catalyst. It retained its activity on repeated use.

EXAMPLE 4

The tube reactor charged with 70 ml of Harshaw tungsten catalyst 0801, ⅛ inch pellets composed of 10% $WO_3$ and 90% $Al_2O_3$, was maintained at 220° C while 50.0 grams per hour of 1,4-butanediol diacetate and 50 ml per hour of water were admitted to the evaporator simultaneously from separate addition funnels. Quantitative glpc analysis of the effluent showed the presence of tetrahydrofuran and acetic acid in 1:2 ratio, with about 5% of the 1,4-butanediol diacetate remaining unconverted. No butanediol or butanediol monoacetate was detected.

It will thus be seen that the objects set forth above among those made apparent from the preceding description are efficiently attained and since certain changes may be made in carrying out the above process and in the composition set forth without departing from the scope of this invention, it is intended that all matters contained in the above description shall be interpreted as illustrative and not in a limiting sense.

What is claimed is:

1. An improved process for producing tetrahydrofuran by heating a carboxylic acid ester of 1,4-butanediol at a temperature of from about 175° C to about 325° C in the presence of water and a catalyst, the improvement comprising using a heterogeneous tungsten oxide catalyst.

2. The process of claim 1 wherein the carboxylic acid ester of 1,4-butanediol is 4-acetoxybutanol.

3. The process of claim 1 wherein the carboxylic acid ester of 1,4-butanediol is 1,4-butanediol diacetate.

4. The process of claim 1 wherein the catalyst is on a support.

5. The process of claim 4 wherein the support is an active support selected from the group consisting of alumina, silica and silica-alumina.

6. An improved process for producing tetrahydrofuran by heating a carboxylic acid monoester of 1,4-butanediol at a temperature of from about 175° C to about 325° C in the presence of a catalyst and under substantially anhydrous conditions, the improvement comprising using a heterogeneous tungsten oxide catalyst.

7. The process of claim 6 wherein the catalyst is on a support.

8. The process of claim 7 wherein the support is an active support selected from the group consisting of alumina, silica, and silica-alumina.

9. The process of claim 6 wherein the carboxylic acid ester of 1,4-butanediol is 4-acetoxybutanol.

* * * * *